United States Patent
Brown

[19]

[11] Patent Number: 5,929,332
[45] Date of Patent: Jul. 27, 1999

[54] SENSOR SHOE FOR MONITORING THE CONDITION OF A FOOT

[76] Inventor: Norma Brown, 2721 Kings Highway, apt. 4M, Brooklyn, N.Y. 11229

[21] Appl. No.: 08/915,535

[22] Filed: Aug. 15, 1997

[51] Int. Cl.[6] .............................. A61B 5/00; A43B 23/00
[52] U.S. Cl. ............................... 73/172; 600/592; 36/136
[58] Field of Search .............................. 73/172; 600/592; 36/136, 139

[56] References Cited

U.S. PATENT DOCUMENTS 5,655,316  8/1997  Huang ................................... 73/172 X

*Primary Examiner*—Harshad Patel
*Assistant Examiner*—Robin C. Clark
*Attorney, Agent, or Firm*—Michael I. Kroll

[57] ABSTRACT

A sensor shoe attached to a power source for sensing conditions of a foot positioned within the sensor shoe. The sensor shoe includes a base, a foot receiving portion extending from the base and an inner sole positioned within the foot receiving portion and atop the base. The inner sole includes a plurality of sensors positioned about an area of the inner sole for sensing conditions within the foot receiving portion and generating signals representative of the sensed conditions. A microcomputer is connected to receive the generated signals from the plurality of sensors and analyzes the signals to determine if a critical situation exists. A medication reservoir containing medication therein is connected to the microcomputer for releasing the medication upon a determination by the microcomputer that a critical situation exists.

11 Claims, 6 Drawing Sheets

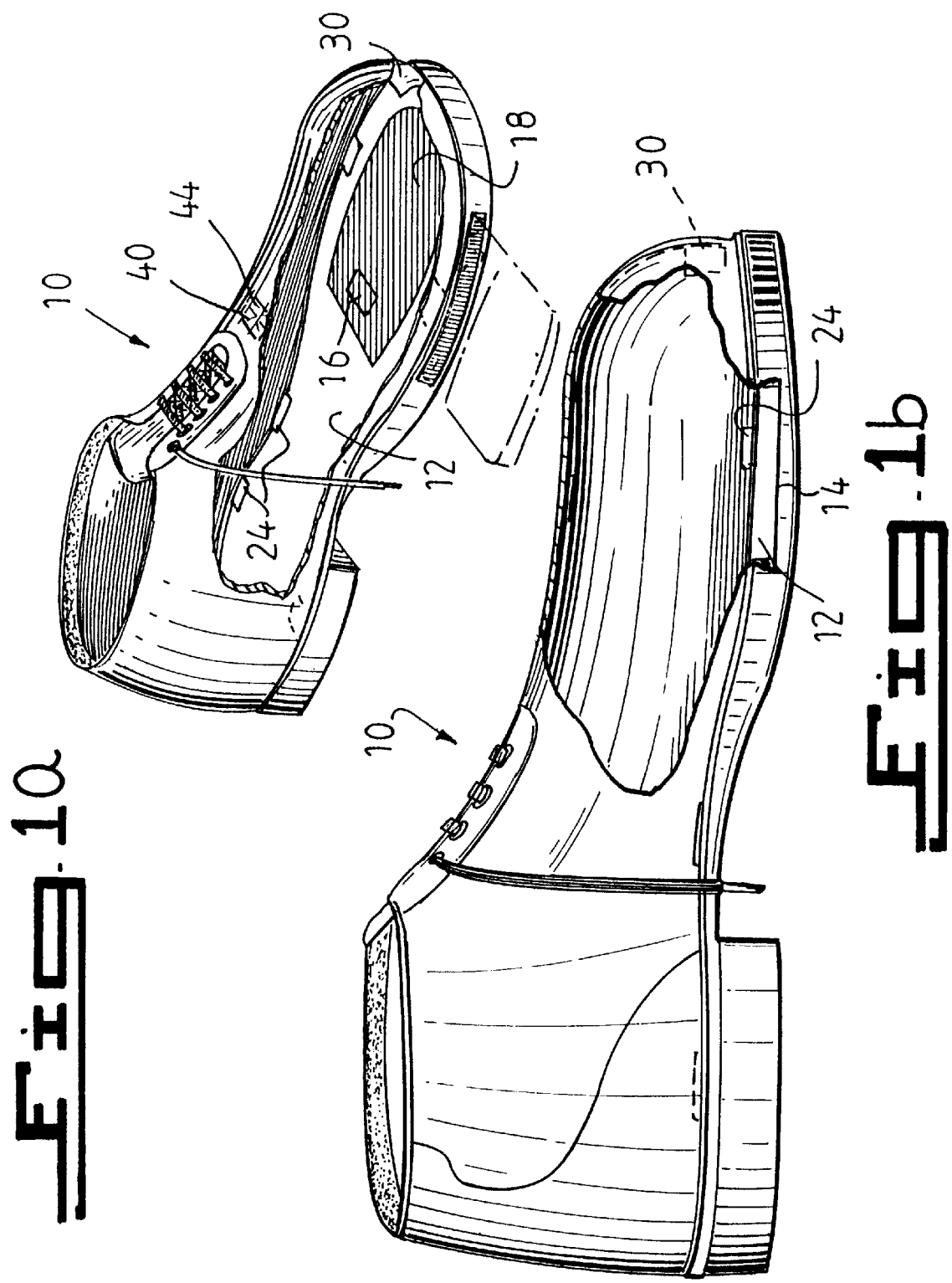

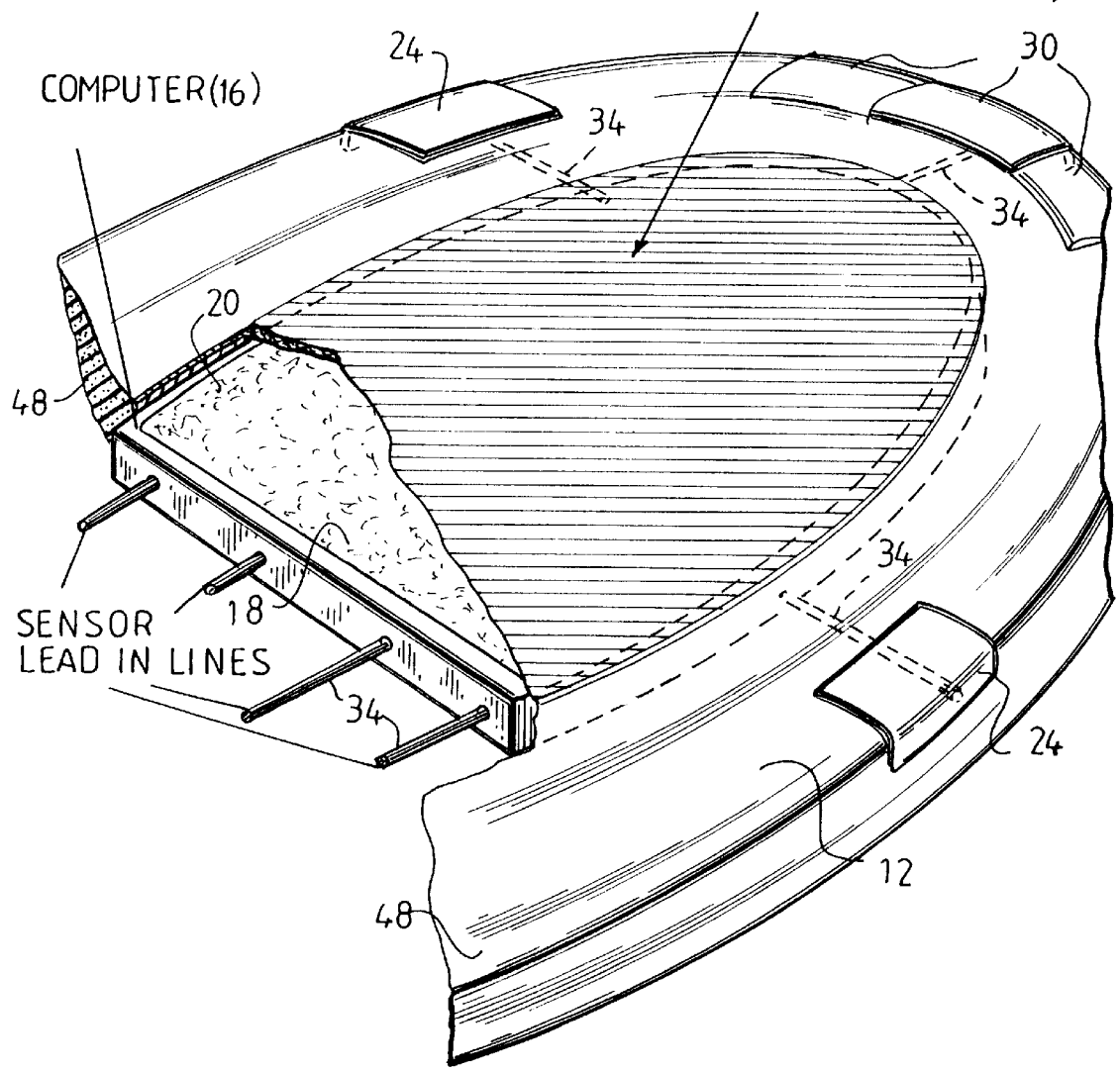

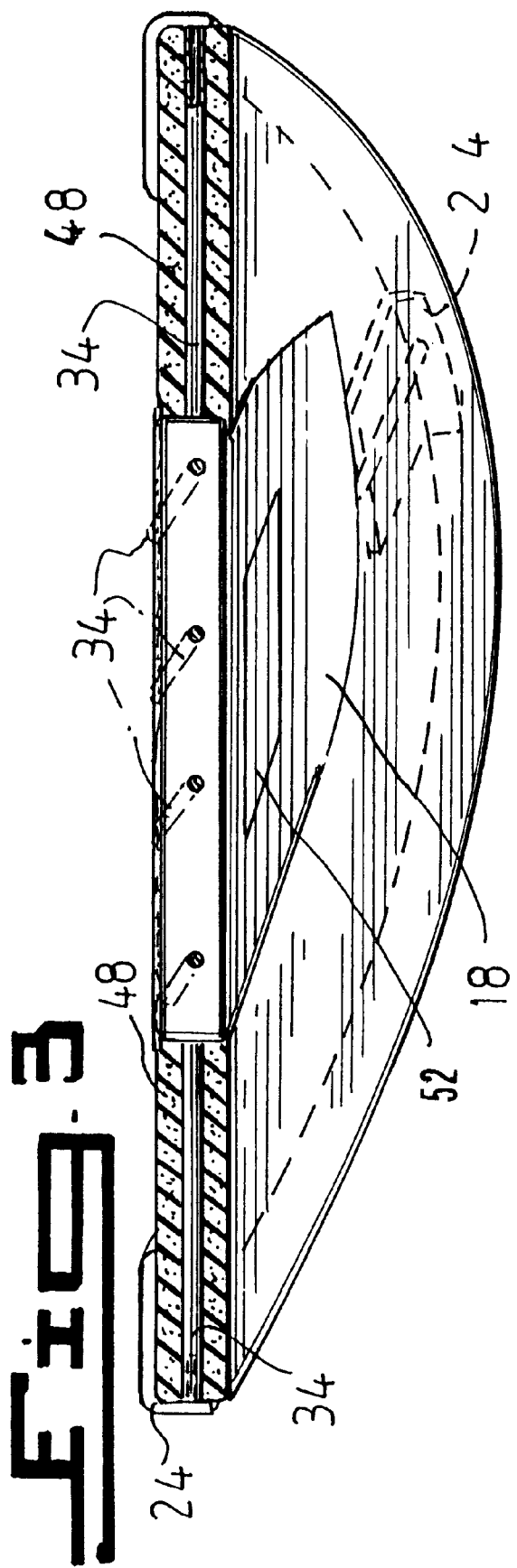

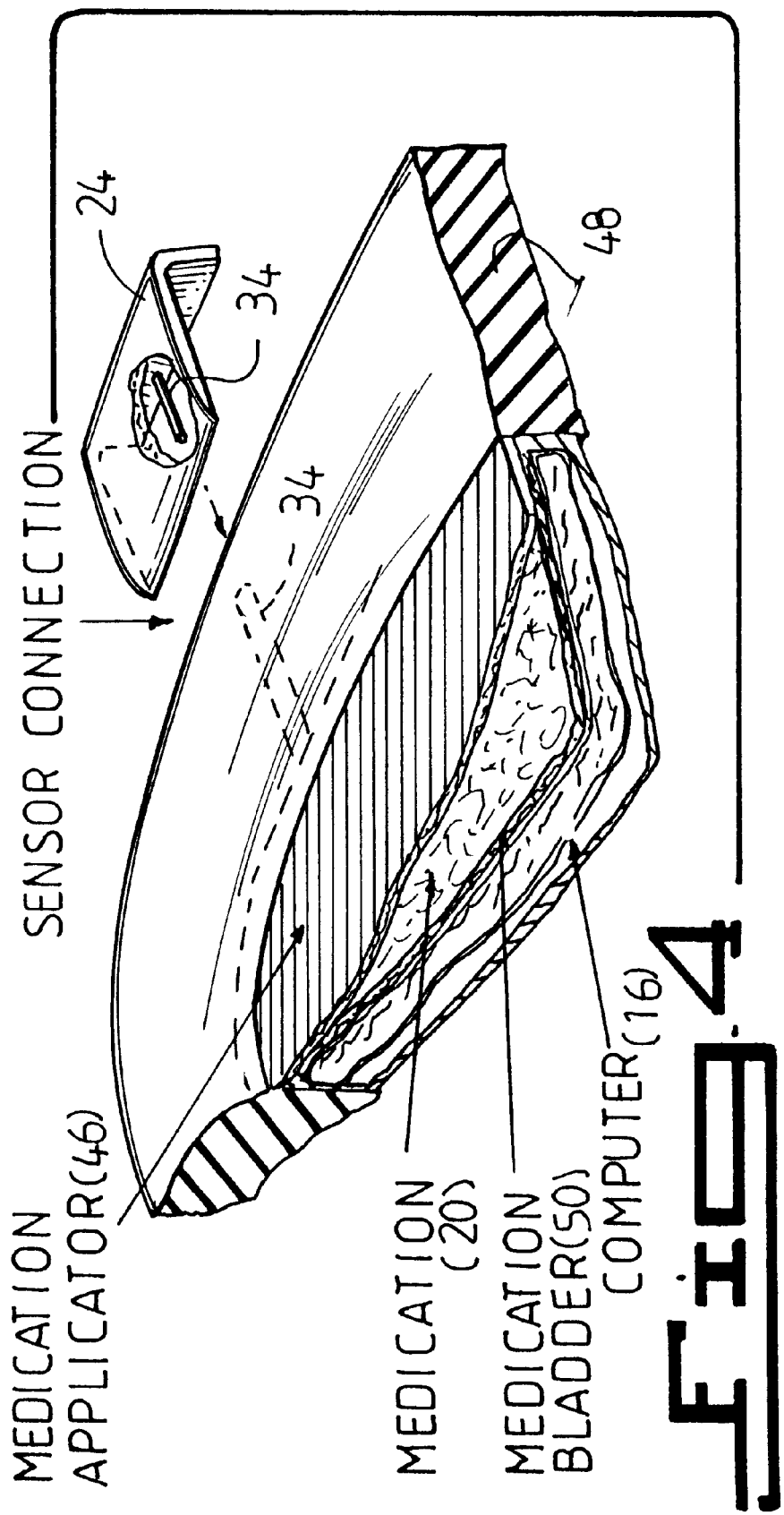

5,929,332

SENSOR SHOE FOR MONITORING THE CONDITION OF A FOOT

BACKGROUND OF THE INVENTION

1. Field of the Invention

The present invention relates generally to shoes and, more specifically, to a shoe including a sensor for detecting foot injury and treating such injury.

2. Description of the Prior Art

Numerous shoes and shoe sensor devices have been provided in the prior art. For example, U.S. Pat. Nos. 5,408,873; 5,566,479; 5,619,186; and 5,642,096 all are illustrative of such prior art. While these units may be suitable for the particular purpose to which they address, they would not be as suitable for the purposes of the present invention as heretofore described.

Foot force sensor for measuring compressive force exerted by a foot. The foot force sensor is in the form of an insole made of layers of relatively thin, planar, flexible, resilient, dielectric material. Electrical contact means having first and second poles and electrical leads extending therefrom is interposed between the layers of the insole. An electrically resistive material is also interposed between the layers of the insole but displaced from the electrical contact means. An electrically conductive interconnecting means is connected between the electrical contact means and the electrically resistive material. The electrically conductive interconnecting means has a plurality of electrically isolated conductive paths laterally displaced from one another and extending through it. The electrically conductive interconnecting means has an electrical resistance which decreases as a compressive force applied to it increases, whereby a closed electrical circuit with shear and hysteresis effects reduced by at least about 20% and with resistance varying with the amount of compressive force applied to the insole is established between the first pole and the second pole of the electrical contact means through the electrically conductive interconnecting means and the electrically resistive material.

A shoe to be worn by diabetic persons, or persons afflicted with various types of foot maladies, where excess pressure exerted upon a portion of the foot tends to give rise to ulceration. The shoe body is fabricated to have relieved areas in the inner surface that contacts the foot at locations where excess pressure is thought to possibly occur. Mounted within each relieved area is a force sensing resistor of a value corresponding to a set threshold, the switching circuit causes the energization of an alarm unit to warn the wearer of the existence of this threshold pressure. At this point in time, the wearer can remove the shoe to prevent the damage to the foot. Provisions can be made to adjust the critical threshold pressure at which the alarm is given.

Device for alarming foot weight capable of operating without restricting an individual's movement. The device comprising a power supply, at least one resistive force sensor, signal conditioning means, calibrating means, programming means and alarm generating means. The alarm generating means generates an alarm when the weight applied to the foot force sensor is at, within or above at least one weight limit or weight range.

A device for prevention of ulcers in the feet of diabetes patients is embodied in a footwear article such as in a shoe. The device includes a sensor disposed in a contained liquid mass of a hydrocell carried in the shoe inner sole, the sensor being one that detects both pressure and temperature values to which the patient's feet are exposed. The sensor includes a bridge circuit comprised of four piezoresistors arranged in two diagonally arrayed pairs, the resistance of one pair of resistors increasing and the resistance of the second pair decreasing in the presence of an increase in the pressure condition in the hydrocell, the resistance of all the resistors increasing or decreasing responsive to respective increases and decreases of temperature in the hydrocell. Outputs from the bridge circuit denotive of respective pressure and temperature values are acquired by a warning signal generator to operate same to generate a patient discernible warning signal that indicates to the patient a need to take action to avoid continuance of exposure to the condition. A grid array sensor detects localized pressure changes on the bottom of the foot by reducing the resistance between conductors present at the location of the increases in pressure. The decreased resistance causes an increase in current flow between the conductors which is detected by a processor which in turn provides an indication of the increased pressure condition.

SUMMARY OF THE PRESENT INVENTION

The present invention relates generally to shoes and, more specifically, to a shoe including a sensor for detecting foot injury and treating such injury.

A primary object of the present invention is to provide a shoe sensor that will overcome the shortcomings of prior art devices.

Another object of the present invention is to provide a shoe sensor which is able to detect chafing of the skin of a wearer of the shoe.

An additional object of the present invention is to provide a shoe sensor including a device for releasing an antibiotic when chafing of the skin is detected.

A further object of the present invention is to provide a shoe sensor which is able to provide an early warning system for treating tissue injury.

A yet further object of the present invention is to provide a shoe sensor which is particularly suited for diabetics.

A still further object of the present invention is to provide a shoe sensor which is able to detect changes in temperature and moisture around the foot of a wearer.

Another object of the present invention is to provide a shoe sensor that is simple and easy to use.

A still further object of the present invention is to provide a shoe sensor that is economical in cost to manufacture.

Additional objects of the present invention will appear as the description proceeds.

A sensor shoe attached to a power source for sensing conditions of a foot positioned within the sensor shoe. The sensor shoe includes a base, a foot receiving portion extending from the base and an inner sole positioned within the foot receiving portion and atop the base. The inner sole includes a plurality of sensors positioned about an area of the inner sole for sensing conditions within the foot receiving portion and generating signals representative of the sensed conditions. A microcomputer is connected to receive the generated signals from the plurality of sensors and analyzes the signals to determine if a critical situation exists. A medication reservoir containing medication therein is connected to the microcomputer for releasing the medication upon a determination by the microcomputer that a critical situation exists.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWING FIGURES

Various other objects, features and attendant advantages of the present invention will become more fully appreciated as the same becomes better understood when considered in conjunction with the accompanying drawings, in which like reference characters designate the same or similar parts throughout the several views.

FIG. 1a is a perspective side view with parts cut away of the shoe sensor of the present invention;

FIG. 1b is a side view with parts cut away of the shoe sensor of the present invention;

FIG. 2 is a top perspective view in partial cross-section of the insole of the shoe sensor of the present invention;

FIG. 3 is a bottom cross-sectional view of a portion of the insole of the shoe sensor of the present invention;

FIG. 4 is a top cross-sectional view of a right corner of the insole of the shoe sensor of the present invention;

DESCRIPTION OF THE REFERENCED NUMERALS

Figure 1:
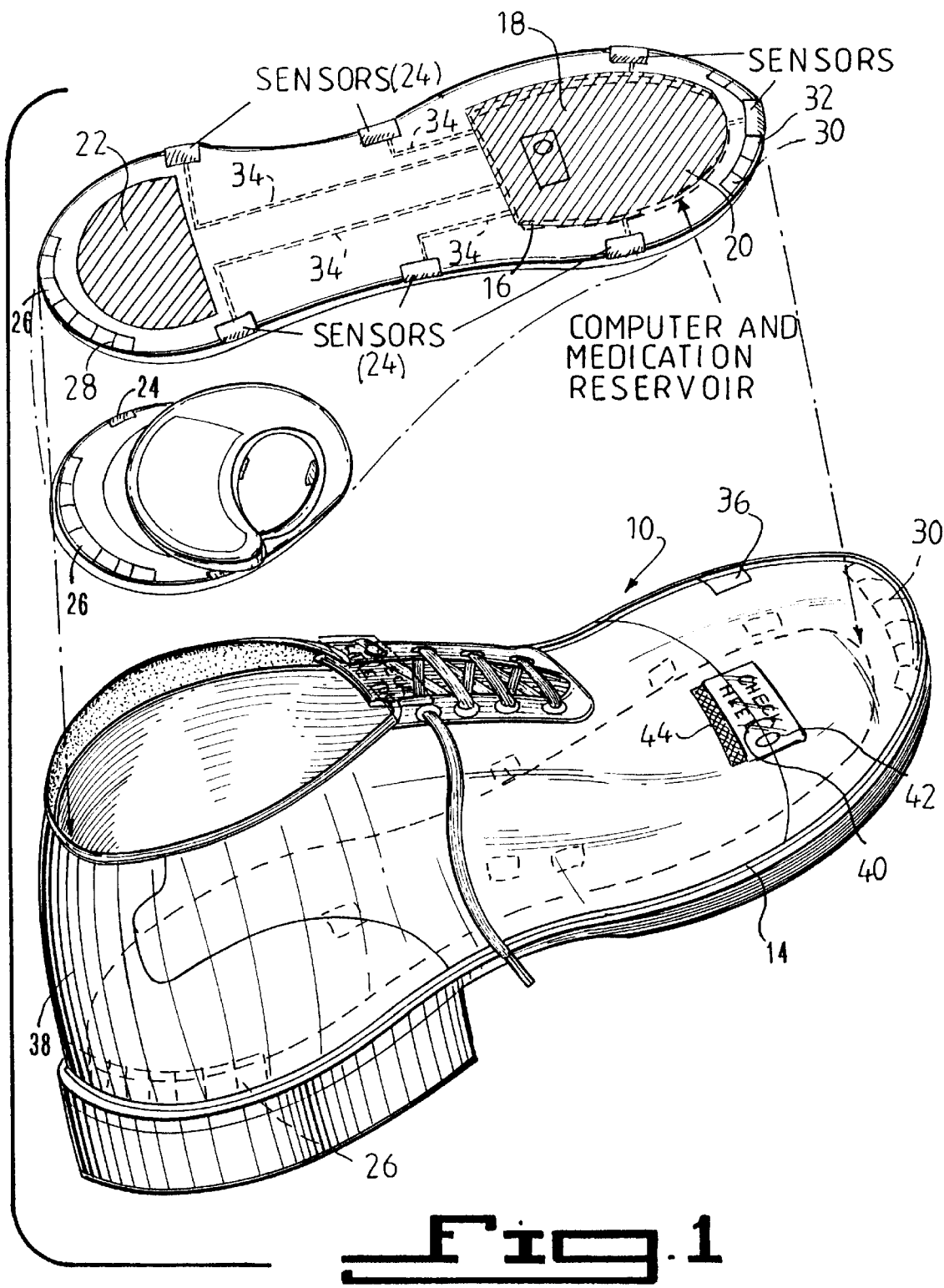
FIG. 1 is an exploded view of he shoe sensor of the present invention illustrating the insole sensor.

Turning now descriptively to the drawings, in which similar reference characters denote similar elements throughout the several views, the Figures illustrate the sensor shoe of the present invention. With regard to the reference numerals used, the following numbering is used throughout the various drawing figures.

10 sensor shoe of the present invention
12 inner sole positioned within sensor shoe of the present invention
14 base of sensor shoe on which inner sole is positioned
16 microcomputer
18 medication reservoir
20 medication
22 heel portion of inner sole
24 plurality of dispersed sensors
26 heel sensors
28 heel of inner sole
30 toe sensors
32 front portion of inner sole
34 lines connecting sensors to microcomputer
36 external temperature sensor
38 outer side of sensor shoe
40 display window
42 visual alarm
44 speaker
46 medication applicator level
48 border surface
50 medication bladder
52 power source
54 recess for housing power source
56 latch door for securing power source within recess

DETAILED DESCRIPTION OF THE PREFERRED EMBODIMENT

Turning now descriptively to the drawings, in which similar reference characters denote similar elements throughout the several views, FIGS. 1 through 6 illustrate a sensor shoe indicated generally by the numeral 10.

The sensor shoe 10 is used as a conventional shoe would be and is designed primarily for diabetics and persons having foot problems. The sensor shoe 10 includes an inner sole 12 sized to fit within the sensor shoe 10 and cover a base side 14 of the sensor shoe 10. The inner sole 12 includes a microcomputer 16 and a medication reservoir 18 containing a medication 20 therein. The microcomputer 16 and medication reservoir 18 may be contained in either the front portion of the inner sole 12, in a heel portion 22 of the inner sole 12 or in any other portion of the inner sole 12 or the sensor shoe 10. The only limitation on the placement of the microcomputer 16 and medication reservoir 18 is that it must be able to adequately medicate the foot within the sensor shoe 10 upon a determination by the microcomputer 16 that treatment is needed.

Positioned around a periphery of the inner sole 12 and dispersed throughout its area are a plurality of area sensors 24. The area sensors 24 are able to sense a plurality of conditions including but not limited to temperature, moisture, texture changes in the skin on the foot of the wearer, etc. The positioning of the sensors 24 in this manner allows the entire foot of the wearer to be sensed at all times and thus provide complete monitoring of the conditions of the foot being sensed. A plurality of heel sensors 26 are positioned about the periphery of a heel portion 28 of the inner sole 12 and a plurality of toe sensors 30 are positioned around a periphery of a front portion 32 of the inner sole 12. The heel and toe sensors 26 and 30, respectively are also able to sense a plurality of conditions including but not limited to temperature, moisture, texture changes in the skin on the foot of the wearer, etc. The additional sensors 26 and 30 are positioned in the heel and toe areas of the sensor shoe 10 as these areas are more susceptible to the conditions which require attention and monitoring and thus must be monitored more closely. Each of the sensors 24, 26 and 30 are connected to transmit signals representative of sensed conditions to the microcomputer 16 via respective connection lines 34. The signals being transmitted are indicative of the conditions being monitored by each individual sensor. The microcomputer 16 will analyze these signals and compare these values to certain threshold values and other measured values to determine whether a situation requiring attention exists.

An external sensor 36 for sensing air temperature outside of the sensor shoe 10 is positioned on an outer side 38 of the sensor shoe 10 and also connected to the microcomputer 16. A visual display 40 including a visual alarm 42 such as an LED is also connected to the outer side 38 of the sensor shoe 10 so the wearer may observe the conditions sensed by the sensors 24, 26 and 30 and analyzed by the microcomputer 16 and be visually alerted to any changes in the sensed conditions. If a change in sensed conditions which requires attention is detected, the visual alarm 42 will be activated to alert the wearer. At all other times a message indicating the current sensed conditions will be displayed on the visual display 40. A speaker 44 is also connected to the microcomputer 16 for producing an audible alarm when a condition requiring attention is detected.

The positioning of the inner sole 12 within the sensor shoe 10 is depicted in FIGS. 1a and 1b. FIG. 1a illustrates a top perspective view of the sensor shoe 10 with a portion of the outer side 38 of the sensor shoe 10 cut away to show the inner sole 12 positioned therein. From this figure the positioning of the sensors 24 can be seen as being dispersed throughout the entire area of the inner sole 12 and the toe sensors 30 as being clustered in a front portion of the inner sole 12. A partial cross sectional view is also shown to illustrate a preferred position of the microcomputer 16 and medication reservoir 18 as being below an area of the sensor shoe 10 housing the ball of the foot. A side view illustrating the placement of the inner sole 12 within the sensor shoe 10 is illustrated in FIG. 1b. This figure illustrates that the inner sole 12 is placed in contact with and atop the inner base 14 of the sensor shoe 10. A sensor 24 is also shown connected to the inner sole 12 and projecting above the position of the inner sole 12 towards the foot of the wearer.

An exploded view of the front portion of the inner sole 12 is depicted in FIG. 2. From this view the area sensors 24 and toe sensors 30 can be more clearly seen along with their position about the area of the inner sole 12. The position of the microcomputer 16 with respect to the medication reservoir 18 is also clearly depicted. From this view it can be seen that the microcomputer 16 forms a central section having a pool therein which defines the area of the medication reservoir 18. The medication 20 filling the medication reservoir 18 is positioned within the pool formed by the dimensions of the microcomputer 16. The medication reservoir 18 is further defined on a side opposite the microcomputer 16 by a medication applicator level 46. The medication 20 is selectively applied to the foot of the wearer through the medication applicator level 46. The application of medication to the foot of the wearer through the medication applicator level 46 is controlled by the microcomputer 16 and based upon an analysis of the sensor signals received from the sensors 24, 26 and 30. Surrounding the microcomputer 16 and connecting it to the inner sole 12 is a semi-rigid border surface 48. The semi-rigid border surface 48 must be rigid enough to hold the microcomputer 16 and medication reservoir 18 in position while being flexible enough to bend with the sensor shoe 10 as the wearer walks or runs without inhibiting the mobility of the wearer.

A bottom view of a front section of the inner sole 12 is illustrated in FIG. 3. From this view a cross-section of the semi-rigid border surface can be seen including connection wires 34 extending therethrough to connect the sensors 24, 26 and 30 to the microcomputer 16. The area sensors 24 can be clearly seen while the toe sensors 30 are depicted in dashed lines. Also viewable from this figure is the power source 52 contained within the central area housing the microcomputer 16. The power source 52 is connected to supply power to the microcomputer 16 and to each of the sensors 24, 26 and 30.

A cross-section of the microcomputer/medication reservoir is illustrated in FIG. 4. From this figure it is clearly seen that the microcomputer/medication reservoir includes a plurality of layers. A bottom layer contains the microcomputer 16. Positioned above the microcomputer 16 is a medication bladder 50 which acts to define the boundaries of the medication reservoir 18. Covering the medication bladder 50 is the medication applicator level 46 and the medication is positioned between and contained within a reservoir formed by the medication bladder 50 and medication applicator level 46. The sensors are connected to the border surface 48 and connected to the microcomputer 16 by the lines 34 extending through the border surface 48.

Figure 5:
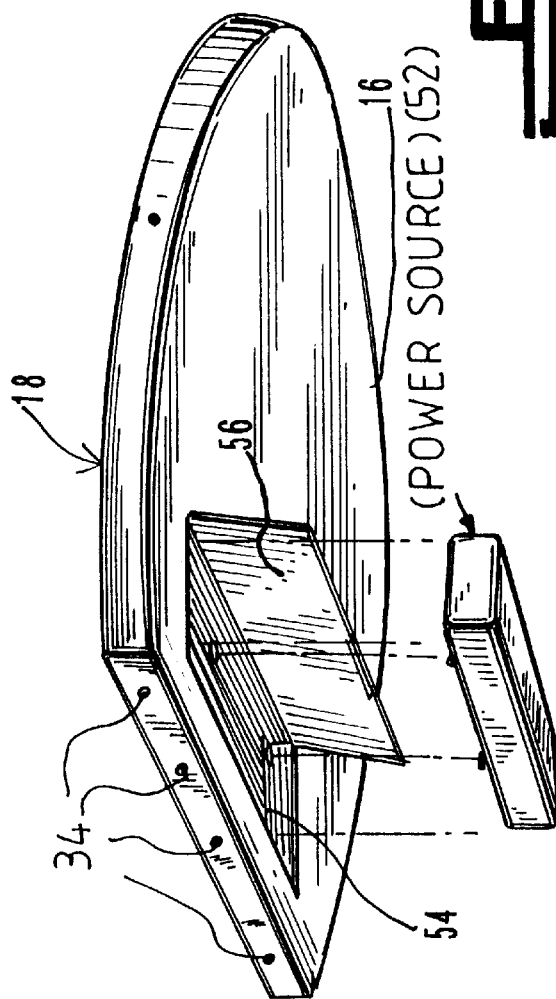
FIG. 5 is a bottom perspective view of a heel portion of the insole of the shoe sensor of the present invention.

The connection of the power source 52 is illustrated in FIG. 5. As can be seen the preferred power source is internally housed with the microcomputer 16 adjacent the medication reservoir 18. The power source 52 may be secured in position within a recess 54 provided therefor by a latch door 56. In this position the power source 52 is able to supply power to all the necessary components, the sensors 24, 26 and 30 receive power through the lines 34.

Figure 6:
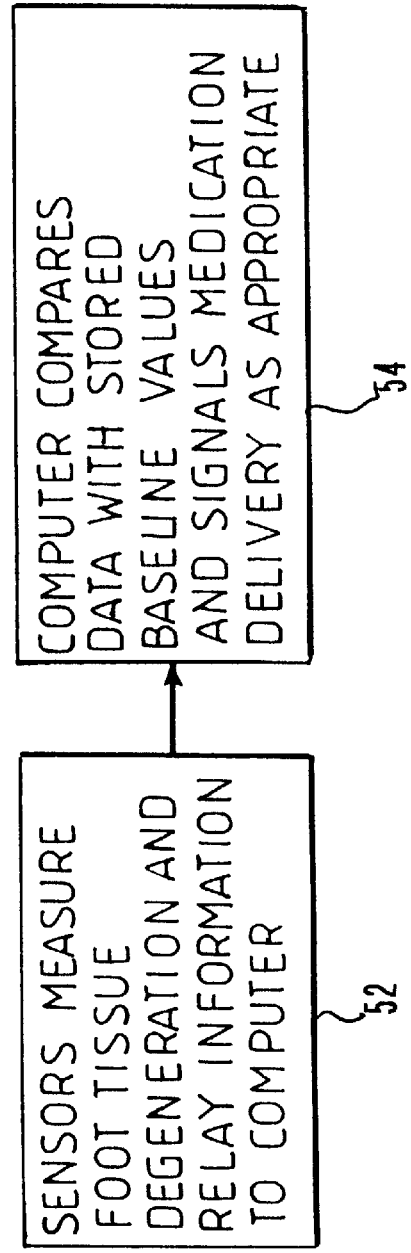
FIG. 6 is a flow diagram illustrating the response of the sensors of the shoe sensor of the present invention.

The operation of the device will now be described with reference to the figures and specifically FIG. 6. In operation, the power source 52 is positioned within the recess 54 and the latch door 56 is closed securing the power source 52 therein. The inner sole 12 is then positioned within the sensor shoe 10 and the sensor shoe is positioned on the foot of a wearer.

The power supplied by the power source 52 activates the sensors 24, 26 and 30 to measure particular conditions within the sensor shoe 10. The sensors 24, 26 and 30 measure foot tissue degeneration and relay the sensed conditions to the microcomputer as stated in step S2. Additional conditions measured by the sensors 24, 26 and 30 include temperature changes and moisture within the sensor shoe 10. An additional sensor 36 measures the temperature outside the sensor shoe 10 and relays this information to the microcomputer 16.

The microcomputer receives the information from the sensors 24, 26, 30 and 36 through the electrical lines 34 and compares the received values with stored base line values to determine if a situation requiring attention exists. If it is determined that a situation requiring attention exists, the microcomputer signals the medication reservoir to release medication through the medication applicator level 46 as appropriate based upon the sensed condition as described in step S4. The continuous sensing of the conditions of the foot continue for as long as the user is wearing the sensor shoe 10 and medication is dispensed To relieve the sensed conditions such as chafing of the skin on the fool during the entire time of use.

From the above description it can be seen that the shoe sensor of the present invention is able to overcome the shortcomings of prior art devices by providing a shoe sensor which is able to detect chafing of the skin of a wearer of the shoe and includes a device for releasing an antibiotic when chafing of the skin is detected. The shoe sensor of the present invention is also able to provide an early warning system for treating tissue injury and is particularly suited for diabetics. Furthermore, the shoe sensor of the present invention is simple and easy to use and economical in cost to manufacture.

It will be understood that each of the elements described above, or two or more together may also find a useful application in other types of methods differing from the type described above.

While certain novel features of this invention have been shown and described and are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims:

1. A sensor shoe attached to a power source for sensing conditions of a foot positioned within said sensor shoe, said sensor shoe comprising a base, a foot receiving portion extending from said base and an inner sole positioned within said foot receiving portion and atop said base, comprising:

a) a plurality of sensors positioned about an area of said inner sole, heel and toes for sensing a number of conditions within said foot receiving portion and generating signals representative of the sensed conditions;

b) a microcomputer connected to receive said generated signals from said plurality of sensors for analyzing said signals by comparing the measured values to certain threshold values to determine if treatment of said foot with medication is required due to existence of a critical situation; and c) a digital display comprising a light emitting diode positioned on the outer side of said foot receiving portion and connected to said microcomputer for displaying a message indicative of the conditions analyzed by said microcomputer, said display including an alarm for indicating a condition requiring attention.

2. The sensor shoe as recited in claim 1, wherein said plurality of sensors include a plurality of area sensors positioned all about a periphery of said inner sole.

3. The sensor shoe as recited in claim 2, wherein said plurality of sensors further include a plurality of toe sensors positioned at a front side of said inner sole for sensing conditions about toes of the wearer.

4. The sensor shoe as recited in claim 3, wherein said plurality of sensors further include a plurality of heel sensors positioned at a back side of said inner sole for sensing conditions about a heel of the wearer.

5. The sensor shoe as recited in claim 4, wherein said plurality of sensors sense degeneration of foot tissue of the wearer.

6. The sensor shoe as recited in claim 5, wherein said plurality of sensors sense a temperature of the foot of the wearer.

7. The sensor shoe as recited in claim 6, wherein said plurality of sensors sense an amount of moisture surrounding the foot of the wearer.

8. The sensor shoe as recited in claim 7, further comprising an outer sensor positioned on an outer side of said foot receiving portion for measuring a temperature outside said foot receiving portion and transmitting a signal indicative of said sensed temperature to said microcomputer.

9. The sensor shoe as recited in claim 1 having a reservoir containing a medication for use when a critical situation exists.

10. The sensor shoe as recited in claim 9 in which said reservoir includes a medication bladder and an applicator.

11. The method of monitoring the foot of a diabetic for foot injury in a shoe comprising the steps of:

a) mounting in said shoe a plurality of sensors for sensing conditions of the foot when positioned within said shoe, said shoe comprising a base and an inner sole positioned atop said base, said plurality of sensors positioned about an area of said inner sole, heel and toes for sensing a number of conditions to which said foot is exposed and generating signals representative of the sensed conditions;

b) installing in said shoe a microcomputer connected to receive said generated signals from said plurality of sensors for analyzing said signals by comparing the measured values to certain threshold values to determine if treatment of said foot with medication is required due to existence of a critical situation;

c) mounting on the outside of said shoe a digital display comprising a light emitting diode positioned on the outer side of said shoe and connected to said microcomputer for displaying a message indicative of the conditions analyzed by said microcomputer, said display including an alarm for indicating a condition requiring attention; and d) inserting said foot into said shoe thereby enabling the monitoring of said foot.

* * * * *